United States Patent [19]
Cobb

[11] Patent Number: 5,771,001
[45] Date of Patent: Jun. 23, 1998

[54] PERSONAL ALARM SYSTEM

[76] Inventor: Marlon J. Cobb, 16332 Oxford Dr., Markham, Ill. 60426

[21] Appl. No.: 749,518

[22] Filed: Nov. 18, 1996

[51] Int. Cl.⁶ .................................................. G08B 23/00
[52] U.S. Cl. .................... 340/573; 340/539; 340/825.08;
340/693; 340/691; 128/690; 128/903; 342/352;
342/357; 455/457; 455/66; 455/67.7; 455/100;
455/556; 455/575
[58] Field of Search ..................................... 340/539, 573,
340/407.1, 825.08, 691, 693; 128/687,
689, 690, 903; 342/42, 44, 350, 352, 357,
450, 451, 458; 455/404, 456, 457, 66, 556,
67.7, 575, 100

[56] References Cited

U.S. PATENT DOCUMENTS

| | | | |
|---|---|---|---|
| 4,086,916 | 5/1978 | Freeman et al. | 128/690 |
| 4,406,290 | 9/1983 | Walbeoffe-Wilson et al. | 128/690 |
| 5,335,664 | 8/1994 | Nagashima | 128/903 |
| 5,408,444 | 4/1995 | Kita et al. | 368/47 |
| 5,497,149 | 3/1996 | Fast | 340/988 |
| 5,627,548 | 5/1997 | Woo et al. | 342/357 |
| 5,652,570 | 7/1997 | Lepkofker | 340/573 |

*Primary Examiner*—Jeffery A. Hofsass
*Assistant Examiner*—Daniel J. Wu

[57] ABSTRACT

A new Personal Alarm System for detecting whether a person is in an emergency situation by measuring blood pressure, pulse and temperature, and thereafter transmitting such information and location through cellular relay stations to a home receiver where the proper authorities may be alerted. The inventive device includes a portable transmitter which transmits an electronic signal through cellular relay stations, and a home receiver which receives the electronic signal and displays the information on an information screen for people at home.

12 Claims, 3 Drawing Sheets

PERSONAL ALARM SYSTEM

BACKGROUND OF THE INVENTION

Field of the Invention

The present invention relates to Personal Security Devices and more particularly pertains to a new Personal Alarm System for detecting whether a person is in an emergency situation by measuring blood pressure, pulse and temperature, and thereafter transmitting such information and location through cellular relay stations to a home receiver where the proper authorities may be alerted.

Description of the Prior Art

The use of Personal Security Devices is known in the prior art. More specifically, Personal Security Devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art Personal Security Devices include U.S. Pat. No. 4,844,091; U.S. Pat. No. 5,417,222; U.S. Pat. No. 5,365,217; U.S. Pat. No. 4,952,928; U.S. Pat. No. 4,670,739 and U.S. Pat. No. 5,003,294.

While these devices fulfill their respective, particular objectives and requirements, the aforementioned patents do not disclose a new Personal Alarm System. The inventive device includes a portable transmitter which transmits an electronic signal through cellular relay stations, and a home receiver which receives the electronic signal and displays the information on an information screen for people at home.

In these respects, the Personal Alarm System according to the present invention substantially departs from the conventional concepts and designs of the prior art, and in so doing provides an apparatus primarily developed for the purpose of detecting whether a person is in an emergency situation by measuring blood pressure, pulse and temperature, and thereafter transmitting such information and location through cellular relay stations to a home receiver where the proper authorities may be alerted.

SUMMARY OF THE INVENTION

In view of the foregoing disadvantages inherent in the known types of Personal Security Devices now present in the prior art, the present invention provides a new Personal Alarm System construction wherein the same can be utilized for detecting whether a person is in an emergency situation by measuring blood pressure, pulse and temperature, and thereafter transmitting such information and location through cellular relay stations to a home receiver where the proper authorities may be alerted.

The general purpose of the present invention, which will be described subsequently in greater detail, is to provide a new Personal Alarm System apparatus and method which has many of the advantages of the Personal Security Devices mentioned heretofore and many novel features that result in a new Personal Alarm System which is not anticipated, rendered obvious, suggested, or even implied by any of the prior art Personal Security Devices, either alone or in any combination thereof.

To attain this, the present invention generally comprises a portable transmitter which transmits an electronic signal through cellular relay stations, and a home receiver which receives the electronic signal and displays the information on an information screen for people at home.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Personal Alarm System apparatus and method which has many of the advantages of the Personal Security Devices mentioned heretofore and many novel features that result in a new Personal Alarm System which is not anticipated, rendered obvious, suggested, or even implied by any of the prior art Personal Security Devices, either alone or in any combination thereof.

It is another object of the present invention to provide a new Personal Alarm System which may be easily and efficiently manufactured and marketed.

It is a further object of the present invention to provide a new Personal Alarm System which is of a durable and reliable construction.

An even further object of the present invention is to provide a new Personal Alarm System which is susceptible of a low cost of manufacture with regard to both materials and labor, and which accordingly is then susceptible of low prices of sale to the consuming public, thereby making such Personal Alarm System economically available to the buying public.

Still yet another object of the present invention is to provide a new Personal Alarm System which provides in the apparatuses and methods of the prior art some of the advantages thereof, while simultaneously overcoming some of the disadvantages normally associated therewith.

Still another object of the present invention is to provide a new Personal Alarm System for detecting whether a person is in an emergency situation by measuring blood pressure, pulse and temperature, and thereafter transmitting such information and location through cellular relay stations to a home receiver where the proper authorities may be alerted.

Yet another object of the present invention is to provide a new Personal Alarm System which includes a portable transmitter which transmits an electronic signal through cellular relay stations, and a home receiver which receives the electronic signal and displays the information on an information screen for people at home.

Still yet another object of the present invention is to provide a new Personal Alarm System that can be utilized to monitor children's behavior in various places.

Even still another object of the present invention is to provide a new Personal Alarm System that provides peace of mind worrying about loved ones.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
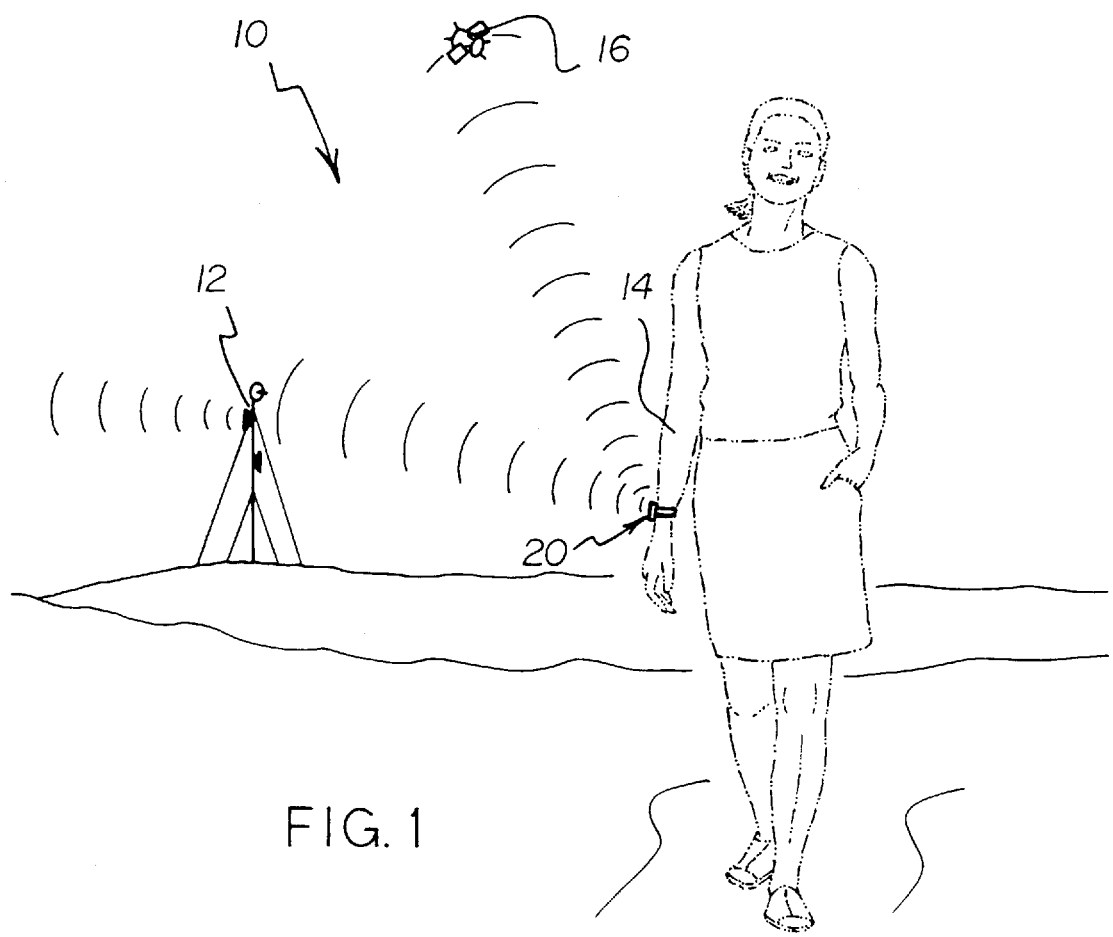
FIG. 1 is a perspective view of a new Personal Alarm System according to the present invention.

With reference now to the drawings, and in particular to FIGS. 1 through 6 thereof, a new Personal Alarm System embodying the principles and concepts of the present invention and generally designated by the reference numeral 10 will be described.

More specifically, it will be noted that the Personal Alarm System 10 comprises a portable transmitter 20 which sends a signal to a cellular relay station, where the signal includes latitude and longitudinal position, pulse, blood pressure, voice, and temperature of the user, and a home receiver 30 which receives the relayed signal from the cellular relay station, thereafter displaying the contents of the signal to viewers at home.

As best illustrated in FIGS. 1 through 5, it can be shown that the portable transmitter 20 includes a transmitter encasement 22. Global positioning receiver 43 is positioned within the transmitter encasement 22. The global positioning receiver 43 determines the position of the user from the signals from a plurality of global positioning satellites 16. Electronic transmitter 41 is positioned within the transmitter encasement 22. The electronic transmitter 41 is electronically connected to the global positioning receiver 43, thereby transmitting the signal to the cellular relay station.

Figure 2:
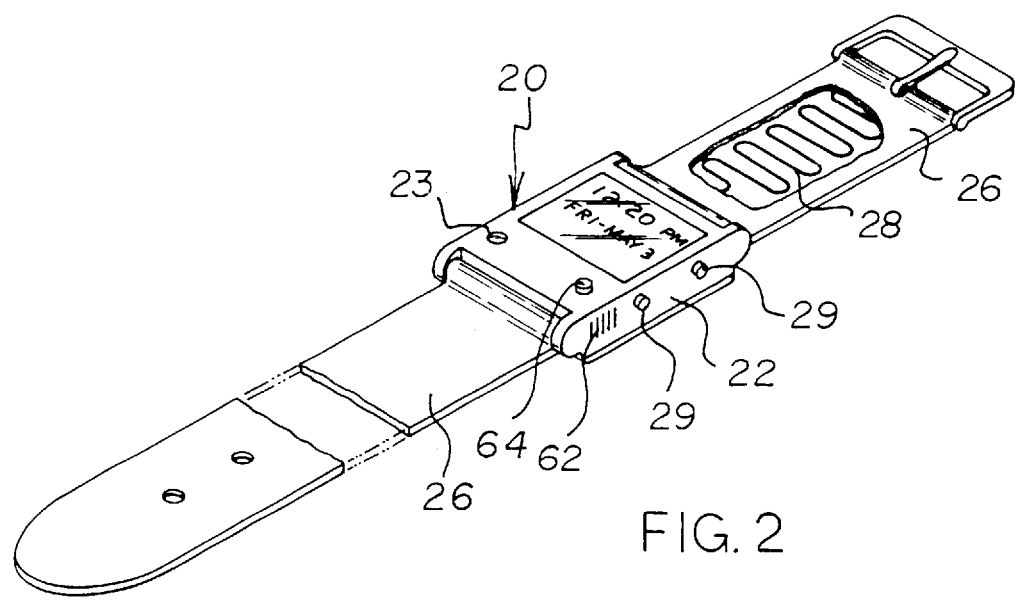
FIG. 2 is an upper perspective view of the portable transmitter.
Figure 3:
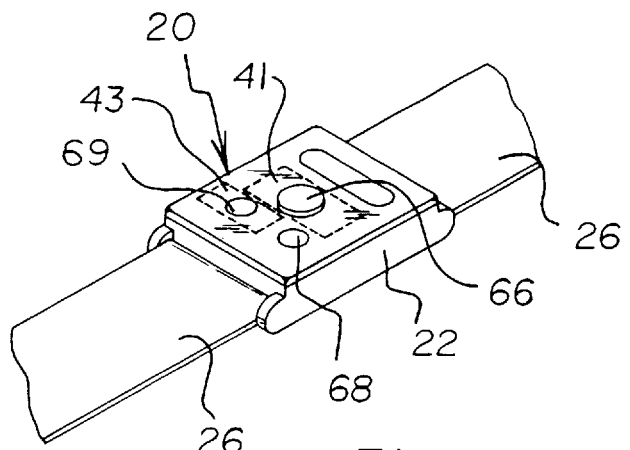
FIG. 3 is a lower perspective view of the portable transmitter.
Figure 4:
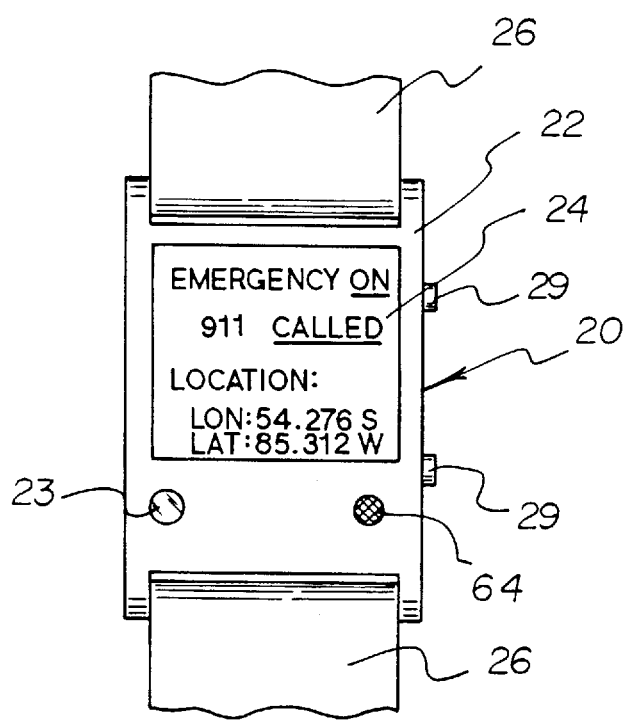
FIG. 4 is a top view of the portable transmitter.
Figure 5:
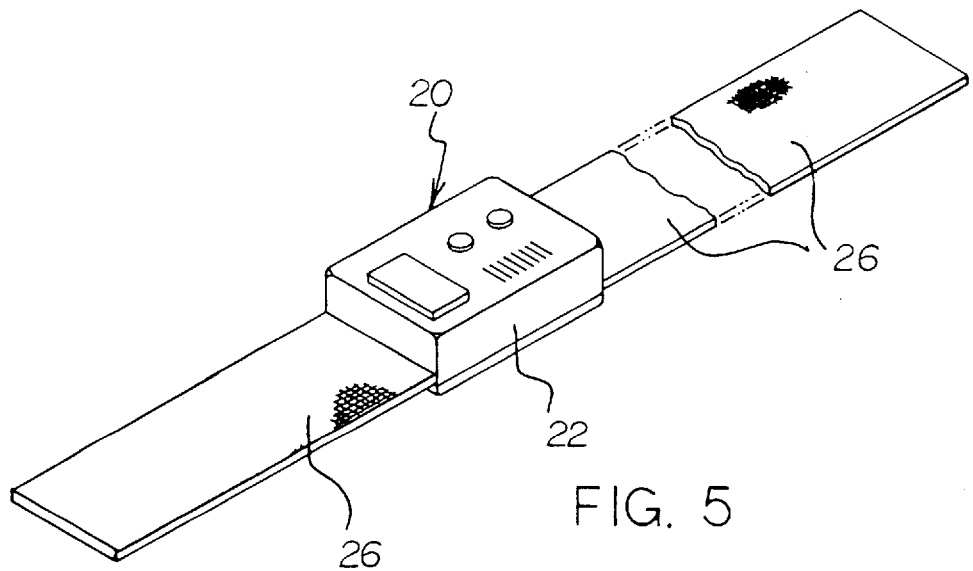
FIG. 5 is a lower perspective view of the portable transmitter.

As best shown in FIG. 4 of the drawings, a display screen 24 is secured to the cornice of the transmitter encasement 22 and electronically connected to the global positioning receiver 43 thereby displaying the latitude and longitudinal information for the user to view. The portable transmitter 20 has a wrist band 26 which removably secures to a user's arm 14 as shown in FIGS. 1–5. An antenna 28 is positioned within the wrist band 26 and electronically connected to the electronic transmitter 41 thereby transmitting the signal to the cellular relay station 12. The portable transmitter 20 has an emergency button 64 electronically connected to the electronic transmitter 41 as best shown in FIG. 4. When the emergency button 64 is pressed twice the electronic transmitter 41 sends the signal to the cellular relay station 12. The portable transmitter 20 has a voice sensor 62 electronically connected to the electronic transmitter 41 as best shown in FIG. 2. A switch 66 is secured to the rear side of the transmitter encasement 22. The switch 66 is electronically connected to the electronic transmitter 41 and activates the electronic transmitter 41 when the transmitter encasement 22 is juxtaposed to the user's arm. A pulse and blood pressure sensor 68 is secured to the rear side of the transmitter encasement 22 and electronically connected to the electronic transmitter 41. A temperature sensor 69 is secured to the rear side of the transmitter encasement 22 and electronically connected to the electronic transmitter 41. The signal transmitted from the electronic transmitter 41 preferably carries longitudinal and latitude position, voice, pulse, blood pressure, and temperature information about the user.

Figure 6:
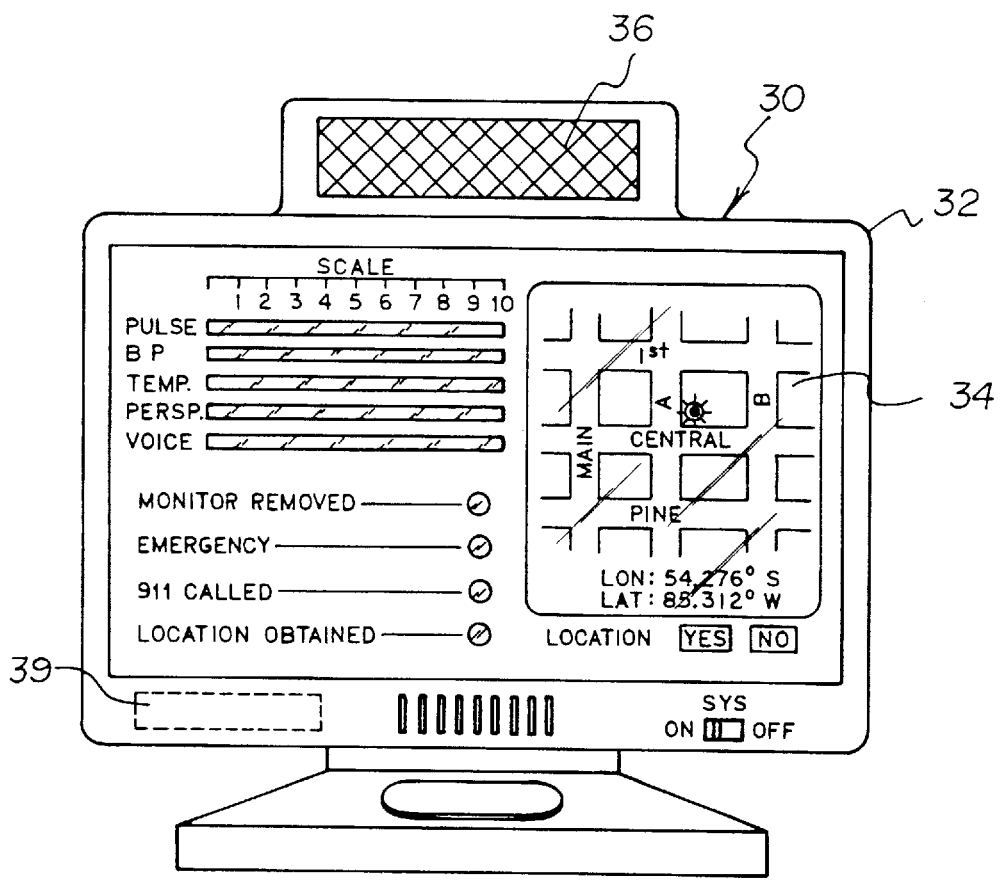
FIG. 6 is a front view of the home receiver.

As shown in FIG. 6 of the drawings, the home receiver 30 has a receiver encasement 32 and an information screen 34 secured to the front of the receiver encasement 32. The home receiver 30 has an electronic receiver 39 which detects and receives the relayed signal from the cellular relay station 12. A speaker 36 is secured to the cornice of the receiver encasement 32 and is electronically connected to the electronic receiver 39 thereby producing an audible alarm when the signal is detected and received. The electronic receiver 39 is electronically connected to the information screen 34 which displays the information carried by the signal. The information screen 34 preferably displays a map of where the wearer of the portable transmitter 20 is located. The portable transmitter 20 includes a plurality of control buttons 29 electronically connected to the electronic transmitter 39.

In use, the user secures the portable transmitter 20 to his arm 14. When the user encounters an emergency situation, he simply presses the emergency button 64 twice. The electronic transmitter 39 sends the longitudinal and latitude position, voice, pulse, blood pressure, and temperature information about the user to the cellular relay station 12. The signal is relayed to the home receiver 30 which displays the information from the signal on the information screen 34 and activates the audible alarm through the speaker 36 to inform persons within the house that the user is in danger and requires assistance. The user may deactivate the signal by pressing the control buttons 29 to enter a special code to prevent false alarms.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by letters patent of the United States is as follows:

1. A personal alarm system comprising:
    a portable transmitter which sends a signal to a cellular relay station, where the signal includes latitude and longitudinal position, pulse, blood pressure, voice, and temperature of the user;
    wherein the portable transmitter includes
        a transmitter encasement,
        a global positioning receiver positioned within the transmitter encasement which determines the position of the user from the signals from a plurality of global positioning satellites,
        an electronic transmitter positioned within the transmitter encasement and electronically connected to the global positioning receiver, thereby transmitting the signal to the cellular relay station, and
        a display screen secured to the cornice of the transmitter encasement and electronically connected to the global positioning receiver thereby displaying the latitude and longitudinal information; and
    a receiver which receives the relayed signal from the cellular relay station, thereafter displaying the contents of the signal.

2. The personal alarm system of claim 1, wherein the portable transmitter includes a wrist band which removably secures to a user's wrist; an antenna is positioned within the wrist band and electronically connected to the electronic transmitter.

3. The personal alarm system of claim 2, wherein the portable transmitter includes an emergency button electronically connected to the electronic transmitter, whereby when the emergency button is pressed twice the electronic transmitter sends the signal to the cellular relay station.

4. The personal alarm system of claim 3, wherein the portable transmitter includes:
    a voice sensor electronically connected to the electronic transmitter;
    a signal light secured to the cornice of the transmitter encasement and electronically connected to the electronic transmitter to display when the signal is being transmitted;
    a switch secured to the rear side of the transmitter encasement, where the switch is electronically connected to the electronic transmitter and activates the electronic transmitter when the transmitter encasement is juxtaposed to the user's arm;
    a pulse and blood pressure sensor secured to the rear side of the transmitter encasement and electronically connected to the electronic transmitter; and
    a temperature sensor secured to the rear side of the transmitter encasement and electronically connected to the electronic transmitter.

5. The personal alarm system of claim 4, wherein the signal transmitted from the electronic transmitter includes longitudinal and latitude position, voice, pulse, blood pressure, and temperature information about the user.

6. The personal alarm system of claim 5, wherein the home receiver includes a receiver encasement and an information screen secured to the front of the receiver encasement.

7. The personal alarm system of claim 6, wherein the receiver includes an electronic receiver which detects and receives the relayed signal from the cellular relay station.

8. The personal alarm system of claim 7, wherein the electronic receiver is electronically connected to the information screen which displays the information carried by the signal and a speaker which emits an audible alarm when the signal is detected and received.

9. The personal alarm system of claim 8, wherein the information screen displays a map of where the wearer of the portable transmitter is located.

10. The personal alarm system of claim 9, wherein the portable transmitter includes a plurality of control buttons electronically connected to the electronic transmitter.

11. A method of monitoring and transmitting the physical state of a person, comprising the steps of:
    (a) securing a portable transmitter to a user's arm which detects the longitudinal and latitude position, voice, pulse, blood pressure, and temperature information of the user;
    (b) transmitting a signal which carries said information to a cellular relay station;
    (c) relaying said information to a home receiver which detects and receives the signal;
    (d) producing an audible alarm through a speaker through the home receiver to warn individuals that the user is in an emergency situation; and
    (e) displaying the information carried by the signal thereby allowing the individuals to determine the location of the user and the user's physical condition.

12. A method of monitoring and transmitting the physical state of a person of claim 11, further comprising the step of electronically calling emergency personal and electronically transmitting the information from the home receiver.

* * * * *